(12) United States Patent
Garzino-Demo

(10) Patent No.: US 6,541,208 B1
(45) Date of Patent: Apr. 1, 2003

(54) DIAGNOSTIC METHOD FOR DISTINGUISHING HIV-ASSOCIATED DEMENTIA FROM OTHER FORMS OF DEMENTIA

(75) Inventor: Alfredo Garzino-Demo, Washington, DC (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 09/042,820

(22) Filed: Mar. 17, 1998

(51) Int. Cl.$^7$ .............................................. G01N 33/53
(52) U.S. Cl. ............................. 435/7.1; 530/351; 435/5
(58) Field of Search ...................................... 435/5, 7.1

(56) References Cited

U.S. PATENT DOCUMENTS

| | | | |
|---|---|---|---|
| 5,459,128 A | 10/1995 | Rollins et al. | 514/8 |
| 5,705,360 A | 1/1998 | Rollins et al. | 435/69.1 |
| 5,739,103 A | 4/1998 | Rollins et al. | 514/8 |
| 5,854,412 A | 12/1998 | Rollins et al. | 536/23.1 |

FOREIGN PATENT DOCUMENTS

| WO | WO 95/13295 | 5/1995 |
|---|---|---|
| WO | WO 96/38559 | 12/1996 |

OTHER PUBLICATIONS

Srongin, W., 1992, "Sensitivity, Specificity, and Predictive Value of Diagnostic Tests: Definitions and Clinical Applications", in *Laboratory Diagnosis of Viral Infections, Second Edition*, E.H. Lennette, ed., Marcel Dekker, Inc., New York, pp. 211–219.*

Beall, C.J. et al., "Site–directed Mutatgenesis of Monocyte Chemoattractant Protein–1 Identifies two Regions of the Polypeptide Essential for Biological Activity," Biochem. J., vol. 313 (1996), pp. 633–640.

Conant, K. et al., "Induction of Monocyte Chemoattractant Protein–1 in HIV Tat–stimulated Astrocytes and Elevation in AIDS Dementia," Proc. Natl. Acad. Sci. USA, vol. 95 No. 6 (1998), pp. 3117–3121.

(List continued on next page.)

*Primary Examiner*—Laurie Scheiner
*Assistant Examiner*—J. S. Parkin
(74) *Attorney, Agent, or Firm*—Marianne Fuierer; Steven J. Hultquist; Yongzhi Yang

(57) ABSTRACT

The HIV-1 transactivator protein Tat significantly increases astrocytic expression and release of monocyte chemoattractant protein-1. Monocyte chemoattractant protein-1 (MCP-1) is expressed in the brains of patients with HIV-1-associated dementia, and is present in the cerebrospinal fluid of patients with this condition. This present invention employs compounds, such as MCP-1 antagonists and partial agonists, as well as HIV-1 Tat-inhibitors in methods for treating and/or preventing HIV-1 associated dementia.

20 Claims, 7 Drawing Sheets

OTHER PUBLICATIONS

Gong, J.H. et al., "An Antagonist of Monocyte Chemoattractant Protein (MCP–1) Inhibits Arthritis in the MRL–1 pr Mouse Model," J. Exper. Med., vol. 186, No. 1 (1997), pp. 131–137.

Gong, J.H. et al., "Antagonists of Monocyte Chemoattractant Protein 1 Identified by Modification of Functionally Critical NH2–Terminal Residues," J. Exper. Med., vol. 181, No. 2, (1995), pp. 631–640.

Rosenzweig, M. et al., "Transductin of CD34+ Hematopoietic Progenitor Cells with an Antitat Gene Protects T–cell and Macrophage Progeny from AIDS Virus Infection," J. Virol., vol. 71, No. 4 (1997), pp. 2740–2746.

Weiss, L., et al., "Plasma Levels of Monocyte Chemoattractant Protein–1 but not Those of Macrophage Inhibitory Protein–1 alpha and RANTES Correlate with Virus Load in Human," J. Infect. Dis., vol. 176, No. 6, 1621–1624.

Berman, et al., "Localization of Monocyte Chemoattractant Peptide–1 Expression in the Central Nervous System in Experimental Autoimmune Encephalomyelitis and Trauma in the Rat," Journal of Immunology 156 (1996) pp. 3017–3023.

Bernasconi, et al. "Selective Elevation of Monocyte Chemotactic Protein–1 in the Cerebrospinal Fluid of AIDS Patients with Cytomegalovirus Encephalitis," The Journal of Infectious Diseases (1996), pp. 1098–1101.

Merrill, et al., "Cytokines in Inflammatory Brain Lesions: Helpful and Harmful," TINS vol. 19, No. 8 (1996), pp. 331–338.

Sasseville, et al., "Chemokine Expression in Simian Immunodeficiency Virus–Induced AIDS Encephalitis," American Journal of Pathology, vol. 149, No. 5, Nov. 1996, pp. 1459–1467.

Schmidtmayerova, et al. "Human Immunodeficiency Virus Type 1 Infection Alters Chemokine β Peptide Expression in Human Monocytes: Implications for Recruitment of Leukocytes into Brain and Lymph Nodes," Proc. Natl. Acad. Sci. USA, vol. 93, Jan. 1996 pp. 700–704.

Sozzani, et al., "MCP–1 and CCR2 in HIV Infection: Regulation of Agonist and Receptor Expression," Journal of Leukocyte Biology, vol. 62, Jul. 1997, pp. 30–33.

Sprenger, et al., "Chemokines in the Cerebrospinal Fluid of Patients with Meningitis," Clinical Immunology and Immunopathology, vol. 80, No. 2, Aug. 1996, pp. 155–161.

* cited by examiner

DIAGNOSTIC METHOD FOR DISTINGUISHING HIV-ASSOCIATED DEMENTIA FROM OTHER FORMS OF DEMENTIA

BACKGROUND OF THE INVENTION

At present, our understanding of the pathogenesis of AIDS-related neurological damage is incomplete. However, monocyte derived cells, included macrophages and microglia, appear to play a critical role in the genesis of this condition. Monocytic infiltration of the central nervous system (CNS) is a cardinal feature of AIDS-related neuropathology as well as a significant correlate of dementia. Monocyte-derived cells are the prime targets for HIV-1 in the CNS. Moreover, such cells have been shown to release a number of substances, which are highly toxic to neurons. These substances include the viral gene products Tat, glycoprotein 41 (gp41) and glycoprotein 120 (gp120), as well as the cellular products tumor necrosis factor-$\alpha$, nitric oxide, platelet activating factor and quinolinate. In vivo studies have shown that many of these toxins are produced predominantly, if not exclusively, by monocyte-derived cells. Also, one study which examined brain tissues from pediatric patients has demonstrated that apoptotic neurons are frequently located in proximity to HIV-1-infected macrophages and microglia.

The present invention makes use of the observation that the HIV-1 Tat protein stimulates the production of monocyte chemoattractant, particularly monocyte chemoattractant protein-1 (MCP-1). MCP-1 is known to be the most potent of a variety of monocyte chemoattractants including RANTES, macrophage inflammatory protein-1$\alpha$ ((MIP-1$\alpha$), MIP-1$\beta$, MCP-2 and MCP-3. MCP-1 is inducible in astrocytes, which are the most numerous cells in the brain.

The HIV-1 encoded transactivator Tat, a soluble protein which is released from HIV-1 infected cells, can increase NF-$\kappa$B binding in astrocytes. We have found that Tat affects astrocytic expression and release of this MCP-1 in a dose dependent manner. MCP-1 is elevated in the CNS of patients with AIDS dementia. AIDS dementia is characterized not only by monocytic infiltration of the brain, but by an increase in Tat encoding transcripts.

SUMMARY OF THE INVENTION

Human astrocytes produce MCP-1, and this production is increased by the HIV-1 protein Tat. The production of MCP-1 is increased in the brains of AIDS patients with dementia.

Unlike RANTES, MIP-1$\alpha$ or MIP-1$\beta$, MCP-1 does not have significant neutralizing activity against primary viral isolates nor does it inhibit HIV-1 infection of microglia. In addition, while MCP-1 may have some antiviral activity under select in vitro conditions in some experiments it has been associated with an increase in HIV-1 replication. Also, like other $\beta$-chemokines, MCP-1 stimulation of select cell types has been associated with increased expression of proinflammatory substances such as interleukin-1$\beta$, interleukin-6 and arachidonate. Moreover, MCP-1 stimulation of monocytes has been associated with an increase in the release of superoxide.

MCP-1 can contribute to the monocytic infiltration that has been observed to correlate with HIVD. Monocytic infiltration in turn can be associated with an increase in the release of neurotoxins. Further, it is likely that a positive feedback loop exists whereby more cells in the brain could be infected, leading to increased levels of Tat and hence more MCP-1.

In transgenic mice, glial-specific expression of MCP-1 is associated with pronounced monocytic infiltration of the CNS. MCP-1 injection into the murine hippocampus also leads to the selective recruitment of monocytes. Additionally, monocyte chemoattractant activity in the CSF of patients with viral meningitis can be inhibited with antibodies to MCP-1.

The concentrations of MCP-1 in the CSF of patients with HIV are sufficient to induce monocyte chemotaxis, and it is possible that local amounts in brain tissue are even higher. Therefore, MCP-1 can play a significant role in the pathophysiology of AIDS dementia. Other chemokines, however, may also be present in association with this condition. For example, brain-derived cells can produce MIP-1$\alpha$, MIP-1$\beta$ and RANTES in vitro. Transcripts of MIP-1$\alpha$, MIP-1$\beta$ and RANTES have been detected in HIVD brain tissues through the use of PCR techniques. However, it is not clear as to whether these chemokines are produced in sufficient quantities to induce chemotaxis.

The HIV-1 Tat protein appears to upregulate the expression of MCP-1 in the CNS of patients with HIVD. Tat is essential for viral replication and, in comparison to HIV-1 structural proteins, is a relatively small diffusible molecule. Once released from infected cells, Tat increases MCP-1 expression, though the exact mechanism is not known. One possible mechanism is that its ability to increase NF-$\kappa$B binding, directly affects MCP-1 expression. At later time points, Tat might also increase MCP-1 expression through indirect mechanisms. For example, Tat could stimulate the production of cytokines that can also induce MCP-1 expression.

The applicant has found that low nanomolar concentrations of Tat were sufficient to increase astrocytic MCP-1 release. These concentrations are slightly lower than those required for gp41 increasing nitric oxide production in mixed neuroglial cultures. Due to the rapid degradation of extracellular protein in autopsy material, as well as cross reactivity of antisera to Tat with endogenous brain proteins, it is difficult to quantitate Tat protein in vivo. However, it has been shown that tat transcripts are elevated in the CNS or AIDS patients with both dementia and encephalitis.

While astrocytes may not be the only CNS cells to produce MCP-1, nor Tat the only stimulus for such production, the ability of Tat to increase astrocytic expression of this chemokine is significant. Not only are astrocytes the most abundant cells in the brain, they are in intimate contact with the blood brain barrier. Such astrocytes could be expected to play an important role in the recruitment of monocytes to the CNS.

The present invention employs the finding that MCP-1 is significantly elevated in the CNS of patients with AIDS dementia in the provision of improved therapies making use of clinically effective inhibitors of MCP-1 and/or its principal receptor CCR-2. These compounds are usefully employed to inhibit the attraction of peripheral monocytes to the CNS even in the presence of stimuli that increase MCP-1 expression. Further, these compounds may be usefully employed to inhibit the activation of monocyte derived cells not only in the CNS but also in the periphery. This invention employs MCP-1 antagonists from other medical fields, such as antagonists used to treat inflammatory conditions such rheumatoid arthritis.

DETAILED DESCRIPTION OF THE INVENTION, AND PREFERRED EMBODIMENTS THEREOF

Figure 1A:
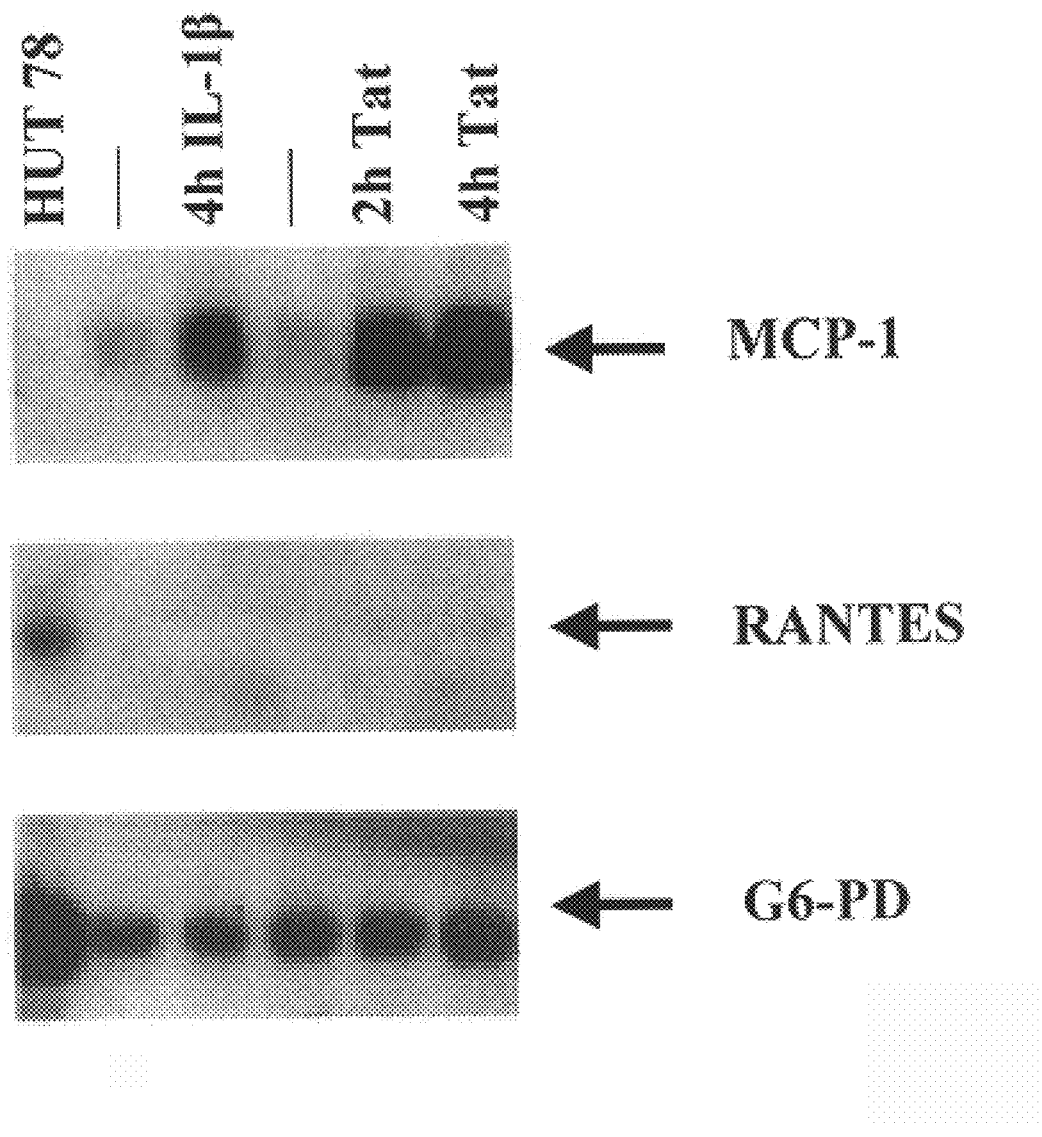
FIG. 1A—Total RNA was extracted from T lymphoblastoid HUT 78 cells (ATCC), and from variously treated human astrocytes. Ten µg per lane were then run on a 1% agarose-6% formaldehyde gel. Following transfer of RNA to nitrocellulose, the blot was probed with the full-length cDNA for MCP-1, and subsequently, RANTES. RNA from untreated astrocytes was run in lanes 2 and 4. Both 4 hr. stimulation with 5 ng/ml interleukin-1β (lane 3) and 2 or 4 hr stimulation with 100 nM Tat (lanes 5 and 6) were associated with an increase in astrocytic MCP-1 expression. Astrocytic expression of RANTES was not detected.

Preparation of Tat Protein and Astrocytes.

Highly purified recombinant $Tat_{1-72}$ was prepared as described in Magnuson et al. (1995). $Tat_{1-72}$ contains the epitope which increases NF-κB binding in astrocytes and was similar to $Tat_{1-86}$ (Intracel) in its ability to increase astrocytic expression of MCP-1.

Cultured Astrocytes.

Brain tissue from 12–14 wk human fetuses was obtained in accordance with NIH guidelines. The tissue was mechanically disrupted by aspiration through a 19-gauge needle, washed in Eagle's minimal essential medium (EMEM) and then distributed into tissue culture flasks. Cells were maintained in EMEM containing 10% fetal bovine serum, 2 mM L-glutamine and 5 µg/ml gentamicin. Several days later, flasks were placed into an orbital incubator shaker at 37° C. and 210 rpm for 6 hr. Non-adherent cells were removed. A portion of the adherent cells were later stained with an antibody to glial fibrallary acidic protein and only those cultures which were >95% positive were used.

RNA Extraction and Northern Blot Analysis.

Total RNA was extracted using RNAzol (Tel-Test) according to the manufacturer's instructions. Prior to RNA extraction, cells were maintained for 6 hr. in serum free media. Northern blot analysis was performed as described previously.

Stimulation of Astrocytes with gp41 and gp120.

Astrocytes ($10^6$ per 1 ml medium) were stimulated with 100 nM HIV-$1_{IIIB}$ gp41 (Intracel) or 100 nM HIV-$1_{IIIB}$ gp 120 (Intracel), and supernatants were assessed 24 hr. later by immunoassay (R&D Systems).

Proliferation Assays.

Astrocytes were grown in 96 well plates. At 70% confluency, cells were treated with varying concentrations of exogenous Tat, in media, which contained 1 µCi per well of tritiated thymidine (New England Nuclear). Twenty-four hr later, cells were washed and harvested onto glass fiber filters. Filters were then dried and placed into scintillation fluid for counting in a Betaplate Apparatus. Twenty hr. following the administration of Tat, in doses from 10–1000 nM, there was no measurable increase in astrocyte proliferation.

Trypsin Digestion.

Trypsin digestion of Tat was performed by the addition of 25 µl of 0.25% trypsin per µg of Tat. The mixture was then incubated for 4 hr. before the 1:1 addition of soybean tripsin inhibitor (Sigma).

Detection of MIP-1α, MIP-1β and RANTES.

MIP1-1α, MIP-1β and RANTES were detected by ELISA (R&D Systems). These ELISAs could detect concentrations as low as 10 pg/ml. Protein measurements were determined by comparison to a standard curve, run in duplicate with each assay.

Immunoabsorption.

Immunoabsorption of Tat was performed as described previously by Magnusson et al. (1995). Briefly, a Tat specific monoclonal antibody (Intracel) was bound to protein A-sepharose (Pharmacia), washed, and then incubated with Tat for 60 min at room temperature, followed by centrifugation.

Cerebral Spinal Fluid (CSF) and Serum Studies.

CSF was obtained from a prospectively characterized population of patients. Computerized tomography or magnetic resonance imaging scans were performed on all patients. Because opportunistic infections of the CNS may influence chemokine expression, those patients with such infections were excluded. Similarly excluded were patients with CNS lymphoma. CD4 cound <200 and/or dementia was the AIDS defining illness in those patients with HIV-1 associated dementia (HIVD). Of the HIV-1 positive patients without dementia (HIV(N)), five had a diagnosis of AIDS as defined by a CD4 count of less than 200 (n=4) or non-CNS opportunistic infection (Candida, n=1_. The CD4 cell counts (number of cells per cubic millimeter) of the HIVD patients (n=10, mean ±S.E.=125±38) were not significantly different from those of HIV(N) patients (n=10, mean ±S.E.= 159±60). The patients' ages, in years, were as follows: HIV: 46+S.E.=9, HIV(N): 34±S.E.=8, multiple sclerosis (MS): 40±S.E.=11, and non-inflammatory neurological (NIN) conditions: 39±S.E.=8. Also, eight patients in each HIV positive group were on antiretroviral therapy at the time of lumbar puncture. Antiretroviral therapy consisted of azidothymidine only (n=4 HIVD and 8 HIV(N)), azidothymidine +lamivudine (n=1 HIVD), lamivudine+stavudine+viramine (N=1 HIVD), or azidothymnidine+lamivudine+saquinavir (n=2 HIVD). In this limited sample size, we could not detect any correlation between triple therapy and CSF MCP-1 values among patients with HIVD. In fact, of the three patients on triple therapy, MCP-1 values were 4279, 1037 and 223 pg/ml.

HIV-1 positive patients were grouped in demented and non-demented according to criteria established by a task force of the American Academy of Neurology.

CSF from 10 patients with clinically definite MS and another 10 patients with noninflammatory conditions of the CNS (headaches or degenerative disc disease) were similarly stored and analyzed.

Analysis of matched serum samples showed that the MCP-1 levels were 2–6 times higher in the SF than in the serum of patients with HIVD. In other groups, the ratio of CSF to serum levels of MCP-1 were between 0.2 and 1.0.

In situ Hybridization Studies.

In situ hybridization was performed on paraffin-embedded brain tissue sections from two HIVD patients, one HIV(N) patient, two patients with MS, and two normal controls. Patients were autopsied at similar postmortem times (12–18 hr). Cause of death was dementia (N=2 HIVD) and interstitial pneumonia (n=1 HIV(N)). Sections from the frontal cortex, hippocampus and brainstem were studied.

In situ hybridization was performed using a $^{33}$P-labeled MCP-1 riboprobe (I.M.A.G.E. consortium no. 488534, homologous to GenBank ID M37719): Prior to use, the probe was sequenced and tested by Northern blot analysis. Negative controls for in situ included in hybridization with the MCP-1 sense strand.

RESULTS

MCP-1 Expression.

Figure 1B:
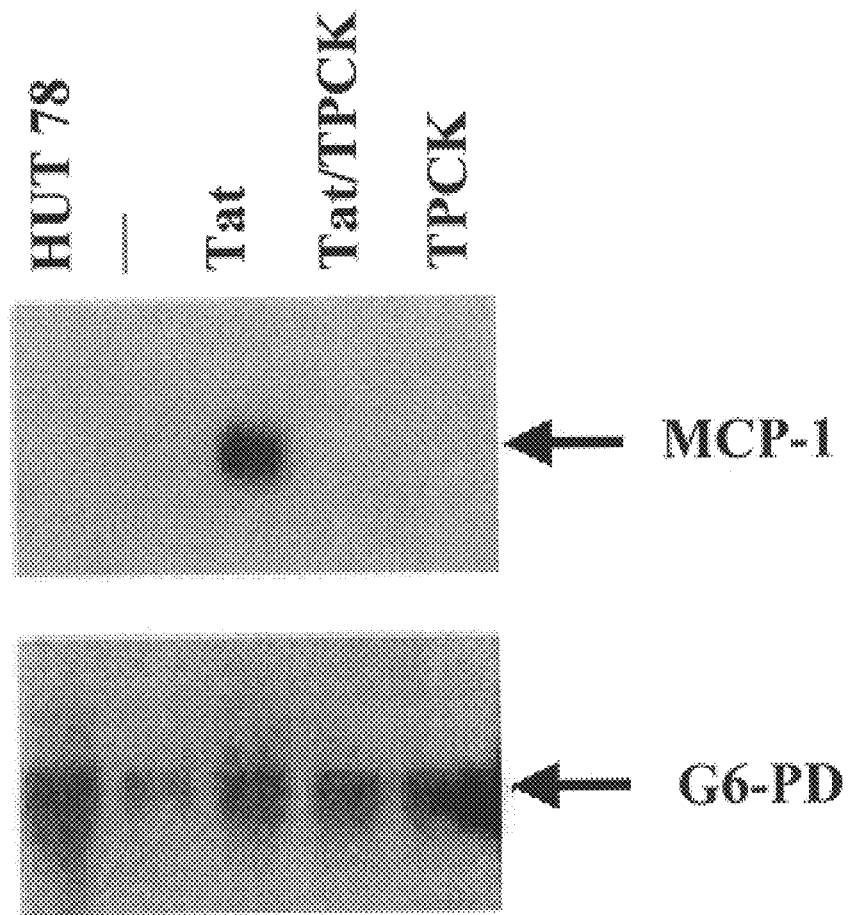
FIG. 1B—Similar experience except that RNA from HUT 78 cells (lane 1) was compared to RNA from astrocytes that were unstimulated (lane 2) or stimulated for 2 hr with 100 nM Tat (lane 3), 25 µM TPCK followed by 100 nM Tat (lane 4) or 25 µM TPCK (lane 5).

To determine whether Tat could increase astrocytic expression of MCP-1, we stimulated astrocytes with 100 nM Tat and then extracted total RNA 2 and 4 hr. later. As demonstrated in FIG. 1, we observed an increase in MCP-1 encoding RNA as early as 2 hr. following stimulation of astrocytes with Tat. Further, consistent with the possibility that NF-κB is required for Tat's effect, we observed that this increase was inhibited by n-tosli-L-phenylalanine chloromethyl ketone (TPCK). This compound blocks the activation of NF-κB by interfering with the degradation of 1-κBα (FIG. 1B).

MCP-1 Protein.

Figure 2A:
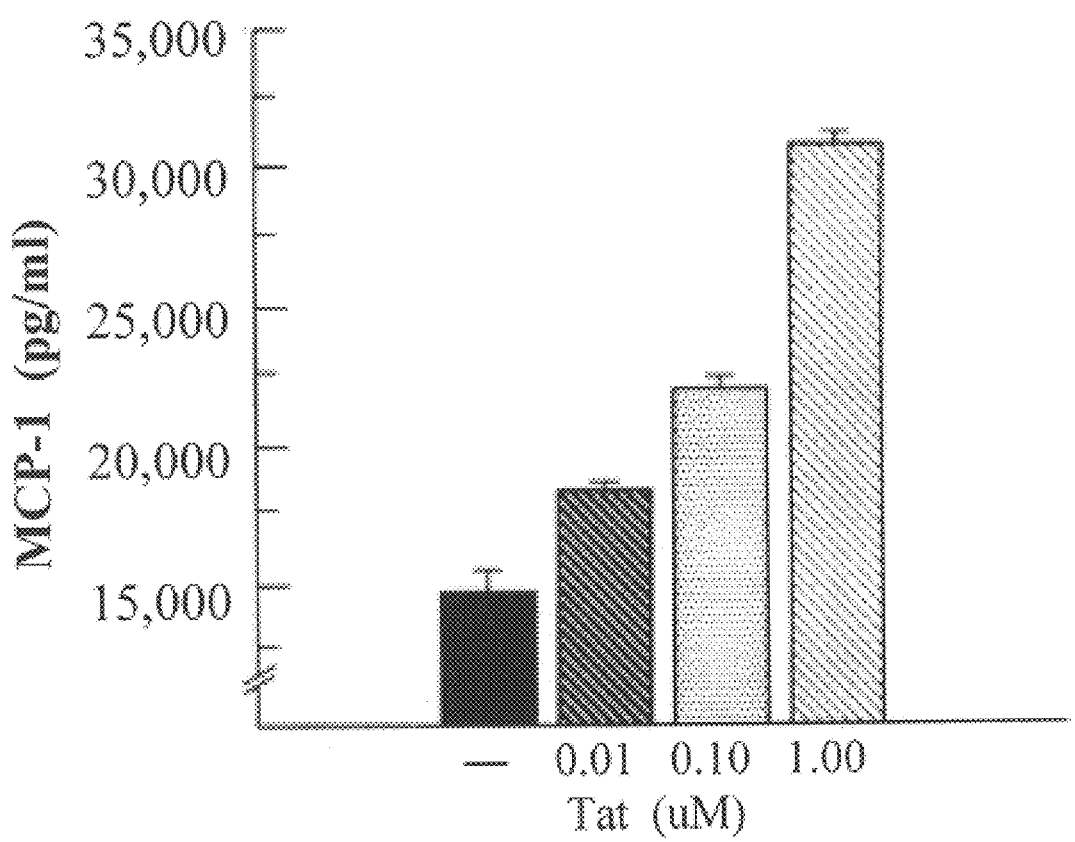
FIG. 2A—Astrocytes were grown to near confluency in 35 cm plates. Each well contained $10^6$ cells in 1 ml medium. Medium was then changed and astrocytes were stimulated with exogenous Tat in doses ranging from 0.01 to 1.0 µM. Twenty hr later, samples were taken for analysis by immunoassay (R&D Systems). As compared to untreated astrocytes (−) which, when grown in tissue culture, express MCP-1 in the absence of stimulation, Tat-stimulated astrocytes showed a significant increase in MCP-1 release. Data are shown as means +S.E. for three replicates.
Figure 2B:
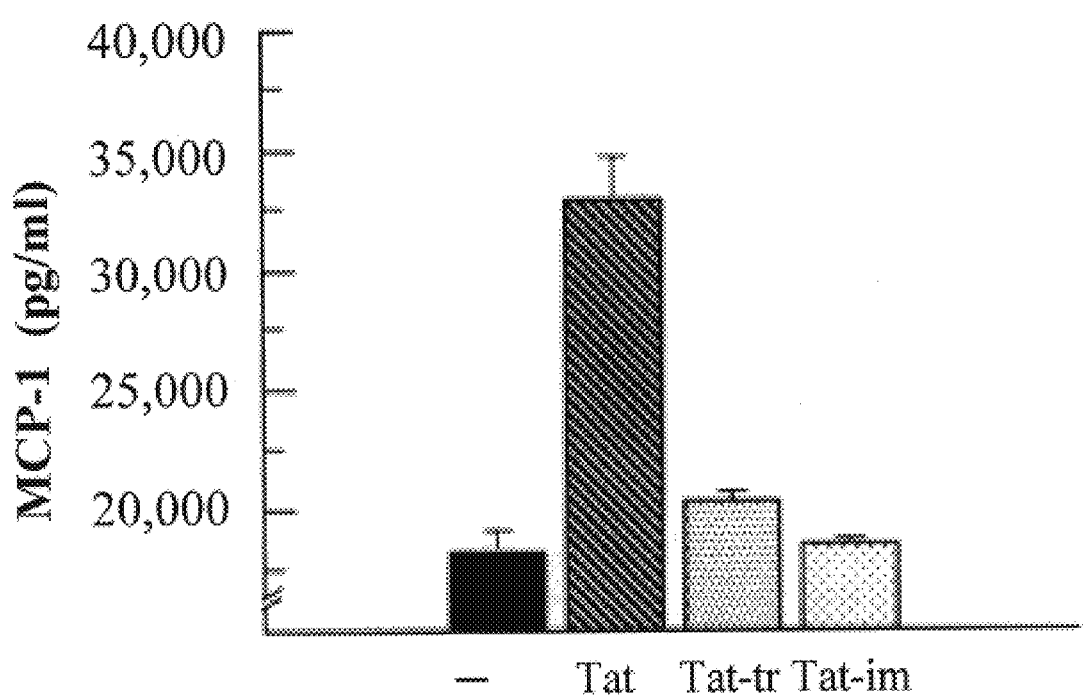
FIG. 2B—Similar experiment except that astrocytes were stimulated with 100 nM Tat or with an equivalent amount of Tat that had first been either digested with tripsin (Tat-tr) or immunoabsorbed (Tat-im).
Figure 3:
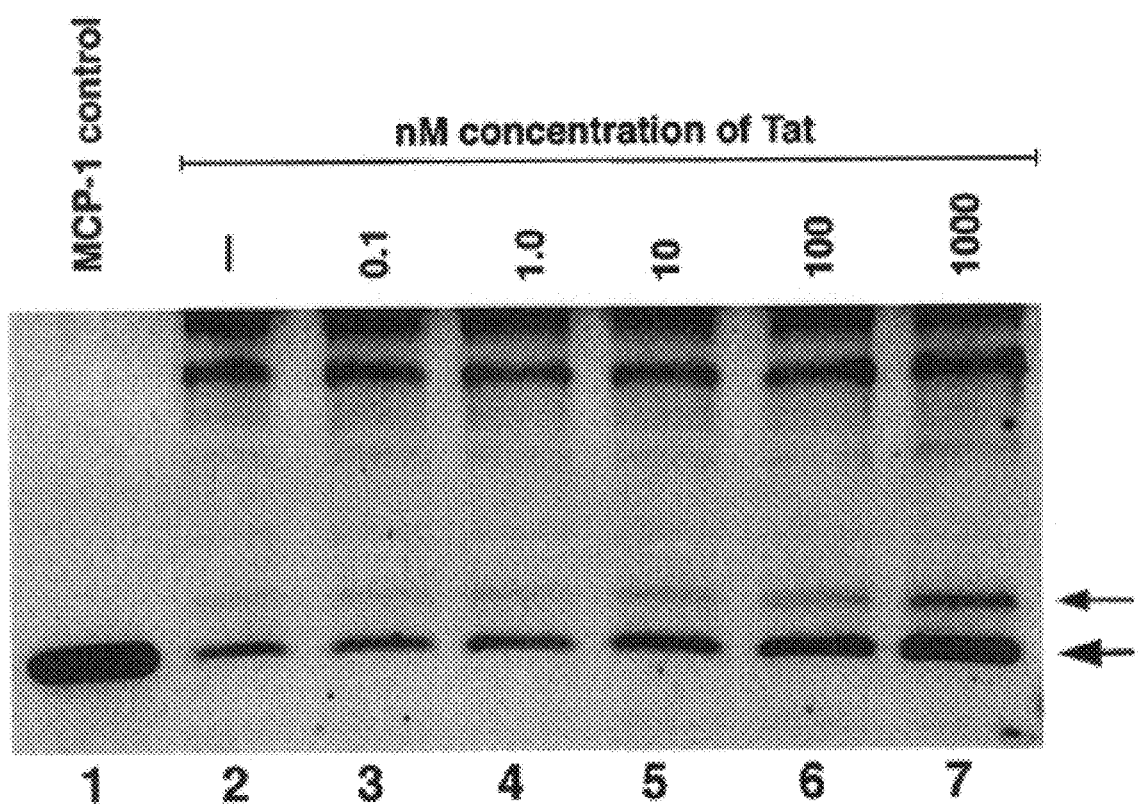
FIG. 3—Western blot analysis of MCP-1 in astrocyte supernatants. In lanes 2–7, 50 µg of protein from variously treated astrocyte supernatants were run on a 15% Tris/Glycine denaturing gel. Three ng of non-glycosylated recombinant MCP-1 (R&D Systems) were run in lane 1 as a control. Following protein transfer to nitrocellulose, the blot was probed with a polyclonal antibody with recognized human MCP-1 (R&D Systems). After washing, an appropriate secondary antibody was applied (horse radish peroxidase conjugated anti-goat, [Santa-Cruz Biotechnology]) and electrochemilurninescence (Amersham) was used to visualize the bands. The two bands, which are specifically increased in association with Tat, are indicated by arrows. The lower arrow represents a band, which runs with an apparent molecular mass of 9 kDa while the upper band, of slighter high molecular mass, is likely to represent MCP-1, which has been altered by the addition of O-linked carbohydrates. Both forms of MCP-1 are active in vitro.

To determine whether increased expression of MCP-1 would correlate with increased protein synthesis or release, we next analyzed the supernatants of Tat treated astrocytes by ELISA and Western blot. As demonstrated in FIGS. 2A and 3, we found that exogenous Tat was associated with a dose-dependent increase in astrocytic release of MCP-1. This increase was specific in that astrocytic release of RANTES, MIP-1α and MIP-1β was not observed. We also determined that neither gp120 nor gp41 had the same effect (not shown). In addition, we found that release of MCP-1 was independent of proliferation, and could be inhibited by either pre-treatment of Tat with trypsin, or immunoabsorption of Tat with a specific antibody (FIG. 1B).

In vivo Studies.

Figure 4:
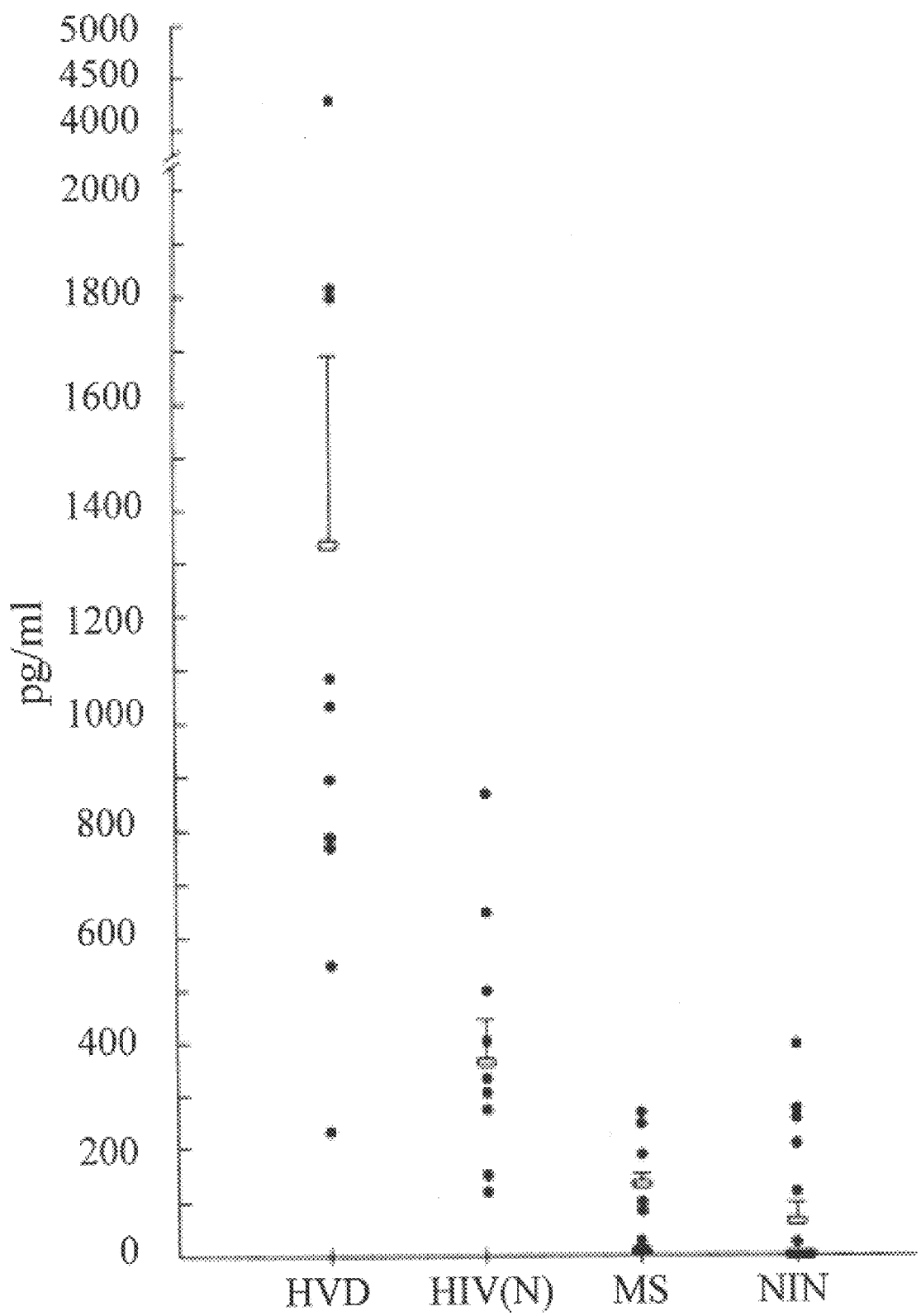
FIG. 4—MCP-1 levels in CSF. MCP-1 levels were analyzed by ELISA (R&D Systems) in CSF samples from HIVD patients (HIVD, n=10), HIV(N) patients (HIV(N), n=10), patients with MS (MS, n=10) and patients with NIN conditions (NIN, n=10). All data are represented as means +S.E. and analyzed by non-parametric analysis using the Mann Whitney test. The comparisons of HIVD to HIV(N), MS and NIN were significant at P<0/002, P<0.002, P<0.001, and P<0.001. The comparisons of HIV(N) to MS and NIN were significant at P<0.01. There were no significant differences between the MS and the NIN groups.

We next examined MCP-1 levels in the CSF of AIDS patients with and without dementia. Both groups of patients had significantly elevated levels of MCP-1 when compared to those patients with MS or NIN conditions. Additionally, patients with HIVD had significantly higher levels of MCP-1 than did HIV(N) patients (FIG. 4). Of note is that the levels of MCP-1 in the CSF of HIVD patients were within the range required to induce monocyte chemotaxis. Also, MCP-1 levels were within the range required to induce monocyte chemotaxis. Also, MCP-1 levels were substantially higher in the CSF as compared to the serum, in HIVD patients. This suggests that MCP-1 was synthesized intrathecally. Simultaneously, we assayed all samples for RANTES, MIP-1α and MIP-1β. RANTES was present in serum samples in concentrations of 1–2 ng/ml. However, these chemokines were below detectable limits (10 pg/ml) in the CSF.

Figure 5:
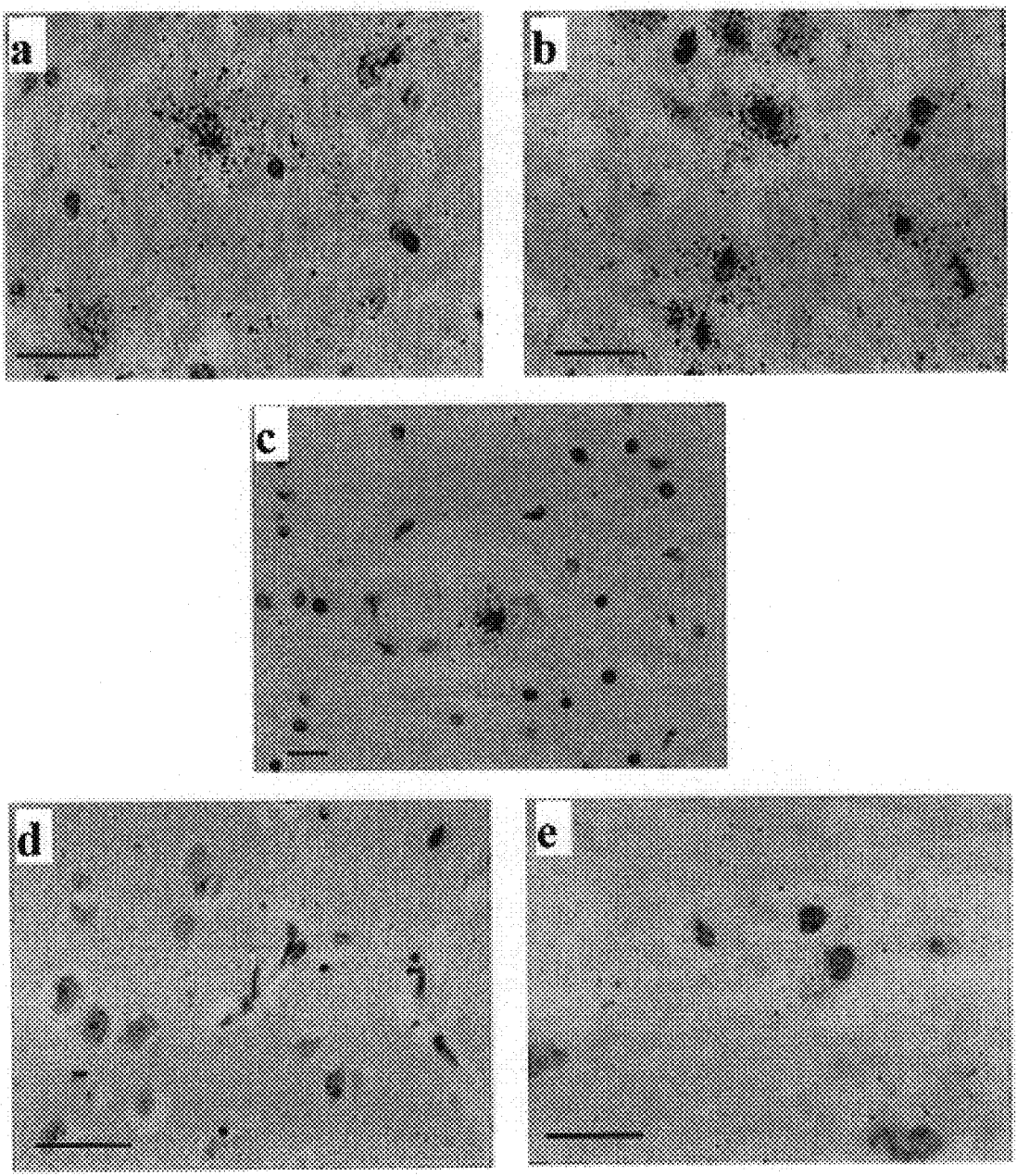
FIG. 5—Detection of MCP-1 RNA in brain tissue by in situ hybridization. Tissue sections were hybridized with an MCP-1 antisense probe. Cells within the cerebral white matter of a HIVD patient show a strong signal for the presence of MCP-1 RNA (a and b). Signal-positive cells are also seen in perivascular regions (c). A representative area from a normal patient shows absence of signal (d) as does a sample from an HIVD patient that was hybridized with an MCP-1 sense probe (e). Scale bars represent 25 µm.

The presence of MCP-1 in the brains of patients with HIVD was further supported by in situ hybridization. Strongly positive cells were noted in several brain regions, including CNS white matter (FIGS. 5(a) and 5(b)). Morphologically, cells were expressed MCP-1 included both astrocytes and neurons. Of interest, cells expressing MCP-1 RNA were often observed in perivascular regions (FIG. 5(c)). In contrast, no positive cells were seen in normal brain tissue or in tissue from patients without dementia (FIG. 5(d)).

The methods of the present invention contemplate the use of a variety of active agents, including MCP-1 antagonists and partial agonists, compounds which inhibit the expression of MCP-1, and compounds which inhibit HIV-1 Tat protein.

Molecules are known in the art which can act as antagonists and/or partial agonists for MCP-1. For example, it is known that an MCP-1 protein with point mutations of Thr-10 to Arg and Tyr-13 to Ile greatly reduced MCP-1 activity. Beal et al. "Site-directed mutagenesis of monocyte chemoattracant protein-1 identifies two regions of the polypeptide essential for biological activity." Biochem J. 313:622–640 (1996) (the disclosure of which is incorporated herein by reference). The present invention contemplates the use of such molecules as antagonists for MCP-1. Such molecules, when administered in therapeutically effective amounts, can inhibit the binding of MCP-1 to its receptors, e.g., to CCR-2, thus reducing the monocyte infiltration that has been observed to correlate with HIV-1 related dementia. Other similar mutations have been described in the art and these can be similarly employed as MCP-1 antagonists.

The methods of the present invention also contemplate the use of MCP-1 inhibitors.

The present invention contemplates the use of any MCP-1 antagonist, e.g., any antagonist that binds to the CCR-2.

The methods of the present invention also contemplate the use of any molecule which prevents expression of MCP-1, e.g., an antisense molecule.

The present invention also contemplates employing MCP-1 as a diagnostic marker for HIV-1 related dementia.

For example, CSF from HIV-1 infected patients can be analyzed by ELISA for the presence of MCP-1. Elevated levels of MCP-1 would be indicative of HIV-1 associated dementia. Similar analysis can be performed on biopsied tissue, such as brain tissue.

Subjects to be treated by the methods of the present invention include both human and non-human animal (e.g., bird, dog, cat, cow, horse) subjects, and are preferably mammalian subjects, and most preferably human subjects.

Depending on the specific condition to be treated, animal subjects may be administered MCP-1 antagonists or inhibitors of MCP-1 expression at any suitable therapeutically effective and safe dosage, as may readily be determined within the skill of the art, and without undue experimentation.

Formulations of the active agents used in the present methods may conveniently be presented in unit dosage forms and may be prepared by any of the methods well known in the art of pharmacy. Such methods generally include the step of bringing the active compound(s) into association with a carrier which constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

It may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The present invention contemplates the employment of the claimed methods in conjunction with antiviral therapies known in the art, and in particular with known single and multi-drug antiviral regimens, e.g., regimens employing zidovudine, didanosine, salcitabine, stavudine, lamivudine, saquinavir, idinavir, and /or ritonavir.

The disclosures of the citations in the following list of references are all incorporated herein by reference.

REFERENCES

1. Price, R. W., Brew. B., Sidtis, J., Rosenblum, M., Scheck, A. C. & Cleary, P. (1988) *Science* 239, 586–592.
2. Glass, J. D., Fedor, H. S., Wesselingh, S. L. & McArthur, J. C. (1995) *Ann. Neurol.* 38, 755–762.
3. Gartner S., Markovits, P., Markovitz, D., Kaplan, M., Gallo, R. & Popovic, M. (1986) *Science* 233, 215–219.
4. Wiley, C., Schrier, R., Nelson, J., Lampert, P. & Oldstone, M. (1986) *Proc. Natl. Acad. Sci. USA* 83, 7089–7093.
5. Koenig, S., Gendelman, H. E., Orenstein, J. M., DalCanto, M. C., Pezeshkpour, G. H., Yungbluth, M., Janofta, F., Aksamit, A., Martin, M. A. & Fauci, A. S. (1986) *Science* 233, 1089–1093.
6. Epstein, L. G. & Gendelman, H. E. (1993) *Ann. Neurol.* 33, 429–436.
7. Magnuson, D. S., Knudsen, B. E., Geiger, J. D., Brownstone, R. M. & Nath, A. (1995) *Ann. Neurol.* 37, 373–380.
8. Adamson, D. C., Wildemann, B., Sasaki, M., Glass, J. D., McArthur, J. C., Christov, V. I., Dawson, T. M. & Dawson, V. L. (1996) *Science* 274,1917–1921.
9. Dreyer, E. B., Kaiser P. K., Offermann, J. T. & Lipton S. A. (1990) *Science* 248, 364–367.
10. Benos, D. J., Hahn, B. H., Bubein, J. K., Ghosh, S. K., Mashburn, N. A., Chaikin, M. A., Shaw, G. M. & Benveniste, E. N. (1994) *Proc. Natl. Acad. Sci. USA* 91, 494498.
11. Toggas, S. M., Masliah, E., Rockenstein, E. M., Rall, G. F., Abraham, C. R. & Mucke, L. (1994) *Nature* 367, 188–193.
12. Gelbard, H. A. & Epstein, L. G. (1995) *Curr. Opin. Pediatr.* 7, 655–662.
13. Gelbard, H. A., James, H., Sharer, L., Perry, S. W., Saito, Y. & Kazee, A. M. (1995) *Neuropathol. Appl. Neurobiol.* 21, 208–217.
14. Bell, M. D., Taub, D. D. & Perry, V. H. (1996) *Neuroscience* 74, 283–292.
15. Graves, D. T. & Jiang, Y. (1995) *Crit. Rev. Oral Biol. Med.* 6, 109–118.
16. Rollins, B. J., Walz, A. & Baggiolini, M. (1991) *Blood* 78, 1112–1116.
17. Uguccioni, M., D'Apuzzo, M., Loetscher, M., Dewald, B. & Baggiolini, M. (1995) *Eur. J. Immunol.* 25, 64–68.
18. Ransohoff, R. M., Hamilton, T. A., Tani, M., Stoler, M. H., Shick, H. E., Major, J. A., Estes, M. L., Thomas, D. M. & Tuohy, V. K. (1993) *FASEB J.* 7, 592600.
19. Berman, J. W., Guida, M. P., Warren, J., Amat, J. & Brosnan, C. F. (1996) *J. Immunol.* 156, 3017–3023.
20. Ensoli, B., Buonaguro, L., Barillari, G., Fiorelli, V., Gendelman, R., Morgan, R. A., Wingfield, P. & Gallo, R. C. (1993) *J. Virol.* 67, 277–287.
21. Conant, K., Ma, M., Nath, A. & Major, E. O. (1996) *J. Virol.* 70, 1384–1389.
22. Ueda, A., Okuda, K., Ohno, S., Shirai, A., Igarashi, T., Matsunaga, K., Fukushima, J., Kawamoto, S., Ishigatsubo, Y. & Okubo, T. (1994) *J. Immunol.* 153, 2052–2063.
23. Wesselingh, S. L., Power, C., Glass, J. D., Tyor, W. R., McArthur, J. C., Farber, J. M., Griffin, J. W. & Griffin, D. E. (1993) *Ann. Neurol.* 33, 576–582.
24. Garzino-Demo, A., Gallo, R. C. & Arya, S. K. (1995) *Hum. Gene Ther.* 6, 177–184.
25. Bernasconi, S., Cinque, P., Peri, G., Sozzani, S., Crociati, A., Torri, W., Vicenzi, E., Vago, L., Lazzarin, A., Poli, G. & Mantovani, A. (1996) *J. Infect. Dis.* 174, 1098–1101.
26. Working Group of the American Academy of Neurology AIDS Task Force. (1991) *Neurology* 41, 778–785.
27. Poser, C. M., Paty, D. W., Scheinberg, L., McDonald, W. I., Davis, F. A., Ebers, G. C., Johnson, K. P., Sibley, W. A., Silberberg, D. H. & Tourtellotte, W. C. (1983) *Ann. Neurol.* 13, 227–231.
28. Henkel, T., Machiedit, T., Alkalay, I., Kronke, M., Ben-Neriah, Y. & Baeuerle, P. A. (1993) *Nature* 365, 182–185.
29. Cocchi, F., DeVico, A. L., Garzino-Demo, A., Arya, S. K., Gallo, R. C. & Lusso, P. (1995) *Science* 270, 1811–1815.
30. He, J., Chen, Y., Farzan, M., Choe, H., Ohagen, A., Gartner, S., Busciglio, J., Yang, Y., Hofmann, W., Newman, W., Mackay, R. C., Sodroski, J. & Gabuzda, D. (1997) *Nature* 385, 645–649.
31. Frade, J. M. R., Liorente, M., Mellado, M., Alcami, J., Gutierrezramos, J. C., Zaballos, A., Deireal, G. & Martineza, C. (1997) *J. Clin. Invest.* 100,497–502.
32. Vicenzi, E., Biswas, P., Mengozzi, M. & Poli, G. (1997) *J. Leukoc. Biol*, 62, 34–40.
33. Sozzani, S. (1994) *Biochem. Biophys. Res. Commun.* 199, 761–766.
34. Azuma, E. K., You, A., Matsushima, T., Kasahara, T., Mizoguchi, H., Saito, M., Takaku, F. & Kitagawa, S. (1996) *Exp. Hemaol.* 24, 169–175.
35. Fuentes, M. E., Durham, S. K., Swerdel, M. R., Lewin, A. C., Barton, D. S., Megill, J. R., Bravo, R. & Lira, S. A. (1995) *J. Immunol.* 155, 5769–57.76.

36. Tani, M. S., Rollins, B. J. & Ransohoff, R. M. (1997) 122$^{nd}$ Ann. Mtg. Am. Neurol. Assoc., San Diego, Calif., p. 97.
37. Lahrtz, F., Piali, L., Nadal, D., Pfister, H. W. Spanaus, K. S., Baggiolini, M., & Fontana, A. (1997) European Journal of Immunology. 10, 2484–2489.
38. Lokensgard J. R., Gekker, G., Ehrlich, L. C., Hu, S., Chao, C. C. & Peterson, P. K. (1997) J. Immunol. 158, 2449–2455.
39. Schmidtmayfrova, H., Nottet, H. S. L. M., Nuovo, G., Raabe, T., Flanagan, C. P R., Dubrovsky, L., Gendelman, H. E., Cerami, A., Bukrinsky, M. & Sherry, F. (1996) Proc. Natl. Acad. Sci. USA 93, 700–704.
40. Rautonen, N., Rautonen,. J., Martin, N. L. & Wara, D. W. (1994) AIDS 8, 1504–1506.
41. Chen, P., Mayne, M., Power, C. &Nath A. (1997) J. Biol. Chem. 272, 22385–22388.
42. Parmentier, H. K., van Wichen, D. F., Mayling, F. H., Goudsmit, J. & Schurman, H. J. (1992) Am. J. Pathol. 141,1209–1216.
43. Wiley, C. A., Baldwin, M. & Achim, C. L. (1996) AIDS 10, 843–847.
44. Premack, B. A. & Schall, T. J. (1996) Nature Med. 2, 1174–1178.
45. Gong, H. J., Ratkay, L. G., Waterfield, J. D. & Clark-Lewis, I. (1997) J. Exp. Med. 186, 131–137.

What is claimed is:

1. A method for distinguishing HIV-associated dementia from a dementia condition which does not cause elevated MCP-1 in CSF, said method comprising determining the level of MCP-1 in a CSF sample obtained from a subject, wherein an elevated level of MCP-1 is diagnostically indicative of HIV-associated dementia.

2. The method according to claim 1 wherein the level of MCP-1 in the CSF is determined using an enzyme-linked immunosorbent sandwich assay.

3. The method of claim 1 wherein the subject is a human.

4. A method for distinguishing HIV-associated dementia in an HIV-infected subject from a dementia condition which does not cause elevated MCP-1 in CSF, said method comprising:
   (a) determining the level of MCP-1 in a CSF sample obtained from the subject;
   (b) determining the level of MCP-1 in a serum sample obtained from the subject;
   (c) comparing the level of MCP-1 in the CSF sample to the level of MCP-1 in the serum sample, wherein an elevated level of MCP-1 in the CSF sample as compared to the level of MCP-1 in the serum sample is diagnostically indicative of HIV-associated dementia.

5. The method of claim 4 wherein the level of MCP-1 in the CSF sample is determined using an enzyme-linked immunosorbent sandwich assay.

6. The method of claim 4 wherein the MCP-1 in the serum sample is determined using an enzyme-linked immunosorbent sandwich assay.

7. The method of claim 4 wherein the subject is a human.

8. A method for distinguishing HIV-associated dementia in an HIV-infected subject from a dementia condition which does not cause elevated levels of MCP-1 in CSF, said method comprising determining the level of MCP-1 in a sample of brain tissue obtained from the subject, wherein an elevated level of MCP-1 in the sample, as compared to a normal level of MCP-1 in a normal population, is diagnostically indicative of HIV-associated dementia.

9. The method of claim 8 wherein the level of MCP-1 in the sample is determined using an enzyme-linked immunosorbent sandwich assay.

10. The method of claim 8 wherein the subject is a human.

11. A method for diagnosing HIV-associated dementia in an HIV-infected subject, said method comprising:
   (a) determining the level of MCP-1 in a CSF sample from the subject; and
   (b) determining the level of one or more other chemokines in a CSF sample from the subject, wherein said other chemokines are selected from the group consisting of RANTES, MIP-1α and MIP-1β, and wherein an elevated level of MCP-1, together with a level of the one or more other chemokines which is below about 10 pg/ml, indicates the presence of HIV-associated dementia.

12. The method of claim 11 wherein the one or more other chemokines comprise MIP-1α.

13. The method of claim 11 wherein the one or more other chemokines comprise MIP-1β.

14. The method of claim 11 wherein the one or more other chemokines comprise RANTES.

15. The method according to claim 11 wherein the level of MCP-1 in the CSF is determined using an enzyme-linked immunosorbent sandwich assay.

16. The method according to claim 11 wherein the level of the one or more other chemokines in the CSF is determined using an enzyme-linked immunosorbent sandwich assay.

17. A method for distinguishing HIV-associated dementia in an HIV-infected subject from a dementia condition which does not cause elevated MCP-1 in CSF, said method comprising:
   (a) obtaining a CSF sample from the subject; and
   (b) determining the level of MCP-1 in the sample, wherein an elevated level of MCP-1 in the sample indicates the presence of HIV-associated dementia.

18. A method for distinguishing HIV-associated dementia in an HIV-infected subject from a dementia condition which does not cause elevated MCP-1 in CSF, said method comprising:
   (a) obtaining a CSF sample from the HIV-infected subject;
   (b) determining the level of MCP-1 in the CSF sample;
   (c) obtaining a serum sample from the HIV-infected subject;
   (d) determining the level of MCP-1 in the serum sample;
   (e) comparing the level of MCP-1 in the CSF sample to the level of MCP-1 in the serum sample, wherein an elevated level of MCP-1 in the CSF sample and a normal level of MCP-1 in the serum sample are indicative of a diagnosis of HIV-associated dementia.

19. A method for distinguishing HIV-associated dementia in an HIV-infected subject from a dementia condition which does not cause elevated MCP-1 in CSF, said method comprising:
   (a) obtaining a sample of brain tissue from the subject;
   (b) determining the level of MCP-1 in the sample, wherein an elevated level of MCP-1 in the sample, as compared a level of MCP-1 in a normal population, indicates a diagnosis of HIV-associated dementia.

20. A method for diagnosing HIV-associated dementia in an HIV-infected subject, said method comprising:
   (a) obtaining a sample of CSF from the subject;
   (b) determining the level of MCP-1 in the sample; and
   (c) determining the level of one or more other chemokines in the sample, wherein said other chemokines are selected from the group consisting of RANTES, MIP-1α and MIP-1β, and wherein an elevated level of MCP-1, together with a level of the one or more chemokines which is below about 10 pg/ml, is diagnostically indicative of HIV-associated dementia.

* * * * *